US012642496B2

(12) United States Patent
Gemmel et al.

(10) Patent No.: US 12,642,496 B2
(45) Date of Patent: Jun. 2, 2026

(54) POSITION MONITORING METHOD AND MEDICAL MOBILE X-RAY DEVICE

(71) Applicant: Siemens Healthcare GmbH, Erlangen (DE)

(72) Inventors: Alexander Gemmel, Erlangen (DE); Martin Oßa Kafentzis, Heroldsberg (DE); Markus Weiten, Nuremberg (DE); Achraf Soulami, Uttenreuth (DE); Randolph Setser, Cornelius, NC (US)

(73) Assignee: Siemens Healthineers AG, Forchheim (DE)

( * ) Notice: Subject to any disclaimer, the term of this patent is extended or adjusted under 35 U.S.C. 154(b) by 242 days.

(21) Appl. No.: 18/370,041

(22) Filed: Sep. 19, 2023

(65) Prior Publication Data

US 2024/0099677 A1     Mar. 28, 2024

Related U.S. Application Data

(60) Provisional application No. 63/409,974, filed on Sep. 26, 2022.

(30) Foreign Application Priority Data

Sep. 29, 2022     (DE) ..................... 10 2022 210 337.8

(51) Int. Cl.
| | |
|---|---|
| *A61B 6/00* | (2024.01) |
| *A61B 6/46* | (2024.01) |
| *G01C 21/16* | (2006.01) |

(52) U.S. Cl.
CPC .......... *A61B 6/4405* (2013.01); *A61B 6/4441* (2013.01); *A61B 6/461* (2013.01); *A61B 6/52* (2013.01); *G01C 21/16* (2013.01)

(58) Field of Classification Search
CPC ... A61B 6/0492; A61B 6/0407; A61B 6/0487; A61B 6/102; A61B 34/20;
(Continued)

(56) References Cited

U.S. PATENT DOCUMENTS

| | | | |
|---|---|---|---|
| 2016/0278732 A1* | 9/2016 | Amiri | ................... A61B 6/547 |
| 2019/0015067 A1 | 1/2019 | Gorges | |

(Continued)

FOREIGN PATENT DOCUMENTS

| | | |
|---|---|---|
| DE | 102011084295 A1 | 4/2013 |
| JP | 2019048034 A | 3/2019 |

(Continued)

OTHER PUBLICATIONS

Wikipedia "Inertiale Messeinheit", (Inertial measurement unit) Screenshot Sep. 27, 2022; (7 pages).

*Primary Examiner* — Irakli Kiknadze
(74) *Attorney, Agent, or Firm* — Lempia Summerfield Katz LLC

(57) ABSTRACT

For checking the positional accuracy, a method for automatically monitoring a position and/or an angle of inclination of a component of a medical mobile X-ray device using at least one inertial measurement unit is provided. The mobile X-ray device has a device trolley and an adjustable C-arm. The at least one inertial measurement unit is arranged on the mobile X-ray device. The method includes: acquiring at least one measured value of the inertial measurement unit; evaluating the at least one measured value of the inertial measurement unit with regard to a position and/or an angle of inclination of the component of the mobile X-ray device; comparing the evaluated position and/or the at least one evaluated angle of inclination with at least one specified value and determining deviations from (Continued)

the at least one specified value; and outputting an indication or a display when the deviation overshoots a threshold value.

18 Claims, 4 Drawing Sheets

(58) Field of Classification Search
CPC ...... A61B 2034/2065; A61B 2090/376; A61B 6/52; A61B 6/547; A61B 6/4441; A61B 6/4405; A61B 6/461; A61B 17/7086; A61B 34/37; A61B 34/10; A61B 34/30; A61B 34/32; A61B 17/708; A61B 2017/564; A61B 2090/3762; A61B 2034/105; A61B 2034/104; A61B 2017/568; A61B 2090/064; A61B 2017/00119; A61B 2560/0437; A61B 2034/108; A61B 2090/3983; A61B 2034/2055; A61B 17/7011; A61B 2090/08021; A61B 2562/0261; A61B 2034/303; A61B 17/17; A61B 17/7001; A61B 2017/681; A61B 2017/00973; A61B 2090/502; A61B 2017/00203; A61B 2017/00207; A61B 34/25; A61B 2090/365; A61B 2090/372; A61B 2090/363; A61B 2090/3764; A61B 2034/2072; A61B 2034/2057; A61B 6/586; A61B 6/584; A61B 6/5205; A61B 6/4464; A61B 6/4085; A61B 90/361; A61B 90/37; A61B 34/70; A61B 17/3403; A61B 5/113; A61B 2090/3945; A61B 2017/00115; A61B 2017/00075; A61B 2017/00199; A61B 2090/3937; A61B 2034/107; A61B 2090/0807; A61B 6/582; A61B 6/12; A61B 2017/00725; A61B 2090/3995; A61B 2090/367; A61B 2034/207; A61B 90/39; A61B 2090/0818; A61B 6/545; A61B 6/56; A61B 6/589; A61B 5/107; A61B 6/466; A61B 6/4482; A61B 6/505; A61B 5/7271; A61B 5/11; A61B 5/742; A61B 6/5294; A61B 2034/2048; A61B 6/5217; A61B 2090/3966; A61B 5/064; A61B 17/7082; A61B 17/00; A61B 90/11; A61B 34/74; A61B 2017/00876; A61B 2034/2051; A61B 2034/302; A61B 2090/0811; A61B 2017/00477; A61B 2017/00699; A61B 2090/034; A61B 17/1757; A61B 2017/00486; A61B 2034/2068; A61B 2505/05; A61B 2034/2061; A61B 6/04; A61B 6/467; A61B 2017/0092; A61B 6/465; A61B 6/548; A61B 5/4571; A61B 5/066; A61B 6/487; A61B 2034/2059; A61B 17/1721; A61B 6/4423; A61B 6/583; A61B 6/4233; A61B 46/10; A61B 17/1703; A61B 90/36; A61B 2034/102; A61B 2017/00902; A61B 2090/3916; A61G 13/02; A61G 2210/50; G01C 21/16; G01C 19/00; G16H 30/40; G16H 40/63; G16H 20/40; G16H 30/20; G06T 7/74; G06T 7/251; G06T 2207/30052; G06T 2207/10016; G06T 2207/30204; G06T 7/70; G06T 7/33; G06T 2207/10072; G06T 2207/10116; G06T 2207/30008; G06T 7/64; G01B 21/042; G01B 15/00; A61F 2/4611; A61F 2/4603; A61F 2002/4632; A61F 2002/4627; A61F 2/4455; A61F 2/4657; A61F 2/4609; A61F 2/34
USPC .......................................................... 378/62
See application file for complete search history.

(56) References Cited

U.S. PATENT DOCUMENTS

| | | | | |
|---|---|---|---|---|
| 2020/0205753 A1 | 7/2020 | Yifat | | |
| 2020/0237336 A1* | 7/2020 | Marino | ................ | A61B 6/547 |
| 2021/0153836 A1* | 5/2021 | Haase | .................. | A61B 6/586 |
| 2022/0386974 A1 | 12/2022 | Hartley | | |
| 2022/0409157 A1 | 12/2022 | Dirckx | | |

FOREIGN PATENT DOCUMENTS

| | | |
|---|---|---|
| WO | 2020142560 A1 | 7/2020 |
| WO | 2021176355 A1 | 9/2021 |
| WO | 2022217291 A1 | 10/2022 |

* cited by examiner

FIG 2

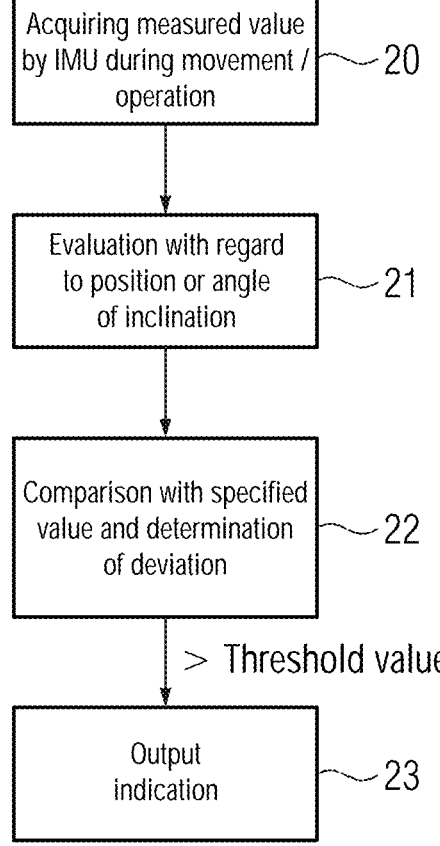

| Acquiring measured value by IMU during movement / operation | ~20 |

Evaluation with regard to position or angle of inclination — 21

Comparison with specified value and determination of deviation — 22

> Threshold value

Output indication — 23

FIG 3

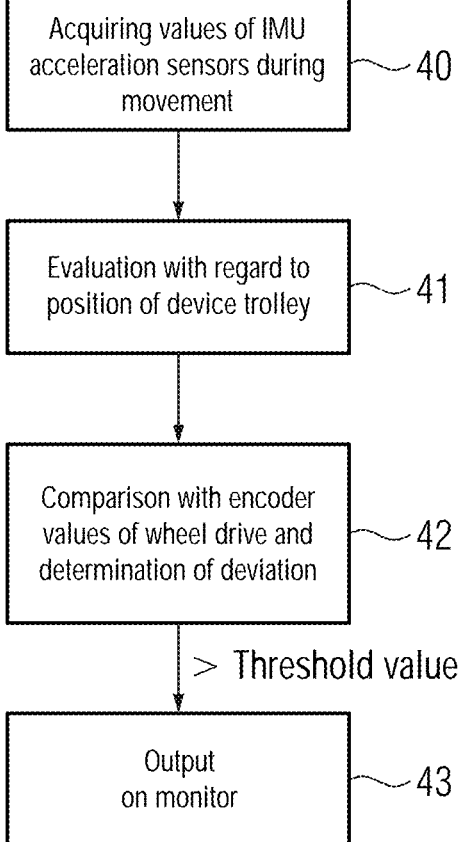

Acquiring values of IMU acceleration sensors during movement — 40

Evaluation with regard to position of device trolley — 41

Comparison with encoder values of wheel drive and determination of deviation — 42

> Threshold value

Output on monitor — 43

FIG 4

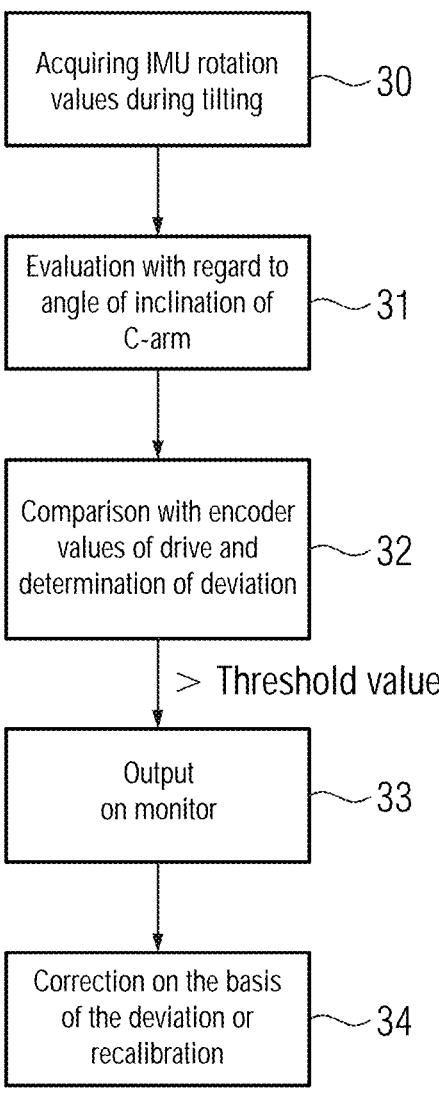

Acquiring IMU rotation values during tilting — 30

Evaluation with regard to angle of inclination of C-arm — 31

Comparison with encoder values of drive and determination of deviation — 32

> Threshold value

Output on monitor — 33

Correction on the basis of the deviation or recalibration — 34

FIG 5

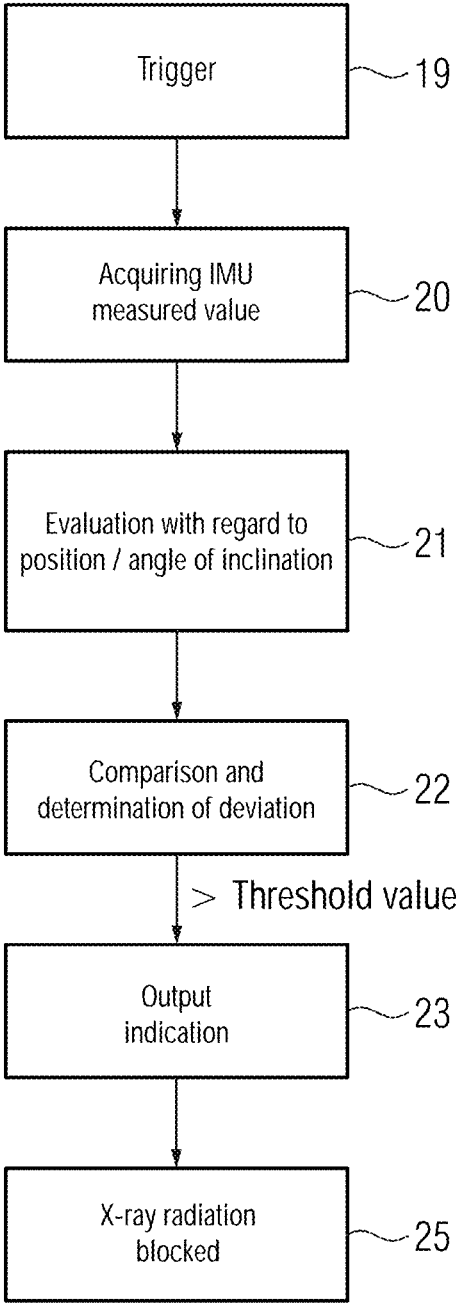

Trigger — 19

Acquiring IMU measured value — 20

Evaluation with regard to position / angle of inclination — 21

Comparison and determination of deviation — 22

> Threshold value

Output indication — 23

X-ray radiation blocked — 25

POSITION MONITORING METHOD AND MEDICAL MOBILE X-RAY DEVICE

The present patent document claims the benefit of U.S. Provisional Patent Application No. 63/409,974, filed Sep. 26, 2022, and German Patent Application No. 10 2022 210 337.8, filed Sep. 29, 2022, which are both hereby incorporated by reference in their entireties.

TECHNICAL FIELD

The disclosure relates to a method for automatically monitoring a position and/or an angle of inclination of a component of a medical mobile X-ray device. The disclosure also relates to a medical mobile X-ray device.

BACKGROUND

Mobile X-ray devices may have a C-arm holding a capture system, which are arranged on a device trolley. The C-arm or its bracket is provided with drives in order to adjust, for example, the angle of inclination, so the capture system may be spatially adjusted in a large number of directions of projection. The device trolley is fitted with wheels on which the mobile X-ray device may be manually moved. In addition, it is known to drive the wheels using a motor in order to firstly enable movement of the device trolley with less force or completely without force, and secondly to automate particular movements of the mobile X-ray device for clinical applications. Modern mobile X-ray devices are used in many fields, for example, for intraoperative imaging in the case of surgical procedures. Apart from single projection images, they are also suitable and may be used for 3D imaging or for panoramic imaging.

In particular, for instances of use of this kind, it is necessary to accurately position the device trolley as well as the capture system in relation to the patient to be treated before each instance of use. A systematic decrease in the positional accuracy between the actuated position and the actual position frequently occurs as a result of various factors, such as vibrations over a relatively long period or due to collisions. Other errors may also occur, (e.g., mechanical inaccuracies), which generate deviations between the actuated position and the actual position. When adjusting the angle of inclination of the C-arm, e.g., the toothed belt that moves the C-arm may skip a tooth without actually adjusting the C-arm, but the movement of the toothed belt is incorrectly assessed as a movement. The details of the movements may be based on items of encoder information from the drives, which are derived from the motorized movement.

In order to prevent such problems, attempts are being made to increase the mechanical stability of the X-ray devices by way of various measures, for example to minimize vibrations or to prevent collisions by way of collision monitoring systems.

SUMMARY AND DESCRIPTION

It is an object of the present disclosure to provide a method that enables, in particular, also long-term stable, exact and error-free positioning of components of a mobile X-ray device. Furthermore, it is an object to provide a suitable mobile X-ray device for carrying out the method.

The object is achieved by a method for automatically monitoring a position and/or an angle of inclination of a component of a medical mobile X-ray device and by a mobile X-ray device as disclosed herein. The scope of the present disclosure is defined solely by the appended claims and is not affected to any degree by the statements within this summary. The present embodiments may obviate one or more of the drawbacks or limitations in the related art.

The method for automatically monitoring a position and/or an angle of inclination of a component of a medical mobile X-ray device, (e.g., of a C-arm), using at least one inertial measurement unit, wherein the mobile X-ray device has a device trolley and a C-arm configured to be adjusted with regard to its position and/or its angle of inclination, and the at least one inertial measurement unit is arranged on the mobile X-ray device is provided herein. The method includes acquiring at least one measured value of the inertial measurement unit. The method further includes evaluating the at least one measured value of the inertial measurement unit with regard to a position or a change in position and/or an angle of inclination or a change in angle of inclination of the component of the mobile X-ray device, e.g., of the C-arm. The method further includes comparing the evaluated position or change in position and/or the at least one evaluated angle of inclination or the change in angle of inclination with at least one specified value and determining deviations from the at least one specified value. The method further includes outputting an indication or a display when the deviation overshoots a threshold value.

By way of the method, it is possible to easily and particularly exactly check by the inertial measurement unit whether the positioning of the component, (for example, of the C-arm or of the device trolley), actually corresponds, for example, to that originally actuated, intended or to values adopted before a disruption or also to the values provided in the operating program or another task and/or whether inaccuracies have occurred.

The method may be carried out, for example, during an adjustment or a movement of the component, for example, for an X-ray photograph. An operator is then made aware of a deviation by way of the indication or the display, so the operator may initiate, for example, appropriate elimination measures before the X-ray photograph is started. Inertial measurement units are very stable in the long term, are easy and uncomplicated to use, may determine positions and orientations quickly and easily, and are very precise. Mobile X-ray devices enable particularly reliable and high-quality imaging by the method. The actuated, provided positions or angles of inclination may be reliably adopted or erroneous details may be corrected, incorrect positionings are minimized. This results in an improved diagnosis. The method also increases patient safety.

In order to acquire six possible kinematic degrees of freedom, known inertial measurement units (IMU) have three acceleration sensors (e.g., translation sensors) that are orthogonal to each other respectively and three angular rate sensors (e.g., gyroscope sensors) mounted orthogonally to each other. The acceleration sensors serve to acquire the translational movement in the x- or y- or z-axis. The angular rate sensors serve to acquire rotating movements in the x- or y- or z-axis, respectively. Three linear acceleration values for the translational movement and three angular speeds for the angular rates are supplied as measured values, see, for example, https://de.wikipedia.org/wiki/Inertiale_Messeinheit. The position(s) and/or the angles of inclination may then be determined from these values by integration.

It is possible to determine very precisely, for example, during a movement (for example, positioning, tilting, translation, travel on a curve, adjustment) of a component of the mobile X-ray device, if required in all three spatial directions, a position or change in position and/or an angle of inclination or a change in angle of inclination of the component by at least one inertial measurement unit.

According to one embodiment, the mobile X-ray device has at least one drive for adjusting the position and/or the angle of inclination of the component and the specified values are based on encoder values of the at least one drive in respect of the position and/or of the angle of inclination of the component. Thus, for example, one or more motor-driven drive(s) are arranged on the wheels of the device trolley for a translational/curving movement or on the C-arm for a tilt/rotation (change in the angle of inclination) or also other movements. Encoder values of such motor-driven drives are customarily used in order to indicate the adopted position from the change or adjustment, to store it or to continue to use it in organ programs. On the basis of the encoder values, the changes are compared during the course of the method with the changes, supplied by the inertial measurement unit, for position and/or angle of inclination and the corresponding deviations are determined. Alternatively, the (absolute or relative) positions or angles of inclination, determined by the encoder values, may also be compared with the (absolute or relative) positions or angles of inclination determined on the basis of the values of the inertial measurement unit. Both possibilities are included below.

According to a further embodiment, the component is formed by the C-arm, the inertial measurement unit is arranged on the C-arm, and the at least one measured value is evaluated with regard to an angle of inclination of the C-arm. In this case, the actual angle of inclination of the C-arm is determined by the inertial measurement unit in one, two, or three spatial direction(s). This is then compared with the angles of inclination obtained from encoder values supplied by the drive(s). For example, the above-mentioned error, (e.g., that the toothed belt incorrectly skips a tooth), may be detected thereby or errors due to vibrations or collisions may also be detected. In such a case, the encoder value supplies, on the basis of the activation of the drive, for example, the information that the toothed wheel was moved (and thereby, for example, the angle of inclination was adjusted by one degree), whereas the inertial measurement unit has not measured a change in the angle of inclination since the toothed wheel has of course actually slipped through. A comparison of either the changes or the resulting absolute angle of inclination then ascertains the corresponding deviation (for example, one degree). An indication, a warning or a display is subsequently output when the deviation overshoots a predefined threshold value (for example, threshold value 0.5°). To be able to correctly evaluate the values of the inertial measurement unit, it is advantageous if the exact geometric ratios of the C-arm relative to the inertial measurement unit are present.

The inertial measurement unit is advantageously arranged indirectly or directly on the X-ray detector. It may be compactly provided, for example, inside the housing of the X-ray detector, here.

The specified values may also be formed by target values input automatically or input by an operator. If, for example, a change in positioning of the device trolley (for example, 50 cm travel in a straight line) or a change in the angle of inclination of the C-arm (for example, 10°) was originally selected therefore, the deviation of these values from the actual positions or changes in position or angles of inclination or changes in angle of inclination, based on the measurements of the inertial measurement unit, is determined and in the case of a deviation which lies above a threshold value, an indication is output.

According to a further embodiment, the X-ray device has a display of the position and/or the angle of inclination of the component of the mobile X-ray device, which display is controlled using the encoder values of the at least one drive. In this embodiment, the method further includes correcting the display based on the deviations and/or recalibration of the encoder values. The starting point is thus, for example, the angle of inclination currently displayed during the course of an adjustment of the C-arm on the basis of the encoder values, which angle continues to be used on a display unit or also in an organ program or another application. If (e.g., owing to a problem, mentioned above, with the toothed wheel or due to degradation as a result of vibrations) this currently displayed angle of inclination does not match the angle of inclination actually reached (and ascertained by the inertial measurement unit), the display or the value used may advantageously be automatically corrected based on the results of the initial measurement unit. Intervention by an operator is thus not necessary. The imaging or image quality dependent on an accurate display or setting of the angle of inclination may be improved or optimized. Additionally, or alternatively, a calibration of the encoder values may also be initiated, so the encoder values may be correctly used again as a future basis.

According to a further embodiment, the component is formed by the device trolley and the inertial measurement unit is arranged on the device trolley, wherein the at least one measured value is evaluated with regard to a position of the device trolley. If, for example, errors occur in the positioning due to vibrations or collisions, these errors may be detected by the method and eliminated or corrected if required. It is also advantageous in this case if the geometric ratios of the device trolley in respect of the inertial measurement unit and potentially other components of the mobile X-ray device are known.

For quickly and clearly informing an operator, the output advantageously includes an acoustic, optical, or haptic warning and/or a display on a display unit, (e.g., monitor, touchpad, or smart device).

According to a further embodiment, the method is automatically triggered by activation of the at least one drive. The corresponding inertial measurement unit starts, (e.g., its measurement at the same time as the drive), so the movements may be registered and a particularly exact measurement results. In particular, the inertial measurement unit measures as long as a movement/adjustment takes place by way of the drive(s).

According to a further embodiment, the specified values are formed by measured values, preliminary to the method, of the inertial measurement unit with regard to a position and/or an angle of inclination of the component of the mobile X-ray device. This may be expedient, for example, in the case of collision monitoring or monitoring with regard to vibrations, in order to establish whether the component has moved as a result of the disruptions. In this case, the IMU may register when a decrease in the positional accuracy occurs. This may be carried out, in particular, such that the acquiring, the evaluating, and the comparing are carried out at least twice in succession with a time interval between them and that the specified values are formed by the measured values of the previous measurement respectively or by a stipulated, preceding measurement.

According to a further embodiment, the deviations are used as the basis for image processing, e.g., a 3D reconstruction or panoramic image processing. In order to increase the image quality, conclusions may be drawn about the differences between the planned and the actual trajectory in the reconstruction of volume images or when combining a plurality of individual projection images (e.g., panoramic imaging). In this way, image processing may be optimized very precisely on the basis of the deviations, and the (2D or 3D) images obtained map the corresponding examination object very accurately.

Advantageously, for unbroken monitoring, the method is carried out continuously as long as the X-ray device is being operated and/or moved. Thus, the effects of vibrations or the effects of the movement of a component on another component (e.g., movement of the device trolley on the angle of inclination of the C-arm) may also be ascertained.

The disclosure also includes a medical mobile X-ray device for carrying out the above-described method. The medical mobile X-ray device includes a device trolley and an adjustable C-arm bracket on which an X-ray detector and an X-ray source are arranged, having at least one inertial measurement unit, which is arranged on the device trolley and/or the C-arm bracket. The inertial measurement unit is configured to acquire sensor data. An evaluation unit of the device is configured to evaluate the sensor data with regard to at least one position and/or an angle of inclination of the device trolley and/or the C-arm bracket. An output unit of the device is configured to output an indication when the deviations overshoot a threshold value and a control unit for actuating the method. A mobile X-ray device of this kind enables particularly reliable and high-quality imaging. The actuated, provided positions or angles of inclination may be reliably adopted, and errors are minimized. This results in an improved diagnosis.

Expediently, the inertial measurement unit is arranged indirectly or directly on the X-ray detector. Advantageously, the inertial measurement unit is arranged indirectly or directly on the device trolley.

A plurality of inertial measurement units may also be present, (e.g., two or three inertial measurement units). In the case of two inertial measurement units, a first inertial measurement unit may be arranged on the device trolley and a second inertial measurement unit may be arranged on the C-arm bracket.

The inertial measurement units may also be used for further measurements, for example, for an automatic calibration of the 0° degree position of the angle of inclination of the C-arm when starting-up the mobile X-ray device. This has previously been carried out manually in that the C-arm is brought into its neutral position using spirit levels, which is then manually confirmed by the operator and the corresponding encoder values are stored and used as a reference. The zero position may be automatically ascertained by using the sensors of the inertial measurement unit and the corresponding encoder values may be stored and used as a reference.

BRIEF DESCRIPTION OF THE DRAWINGS

The disclosure and further advantageous embodiments according to features of the subclaims are explained in more detail in the drawings below with reference to schematically represented exemplary embodiments, without the disclosure being limited to these exemplary embodiments thereby. In the drawings:

FIG. 2 depicts an example of a sequence of acts of the method.

FIG. 3 depicts an example of a further sequence of acts of the method during a movement of a device trolley of the mobile X-ray device.

FIG. 4 depicts an example of a further sequence of acts of the method during a rotational movement of a C-arm of the mobile X-ray device with an additional act.

FIG. 5 depicts an example of a further sequence of acts of the method.

DETAILED DESCRIPTION

When mobile X-ray devices are used for complex applications, such as 3D imaging, panoramic imaging, or intraoperative imaging, it is particularly important to accurately position the device trolley as well as the capture system in relation to the patient to be treated before each instance of use and to correct deficient positional accuracy between the actuated position and the actual position.

Figure 1:
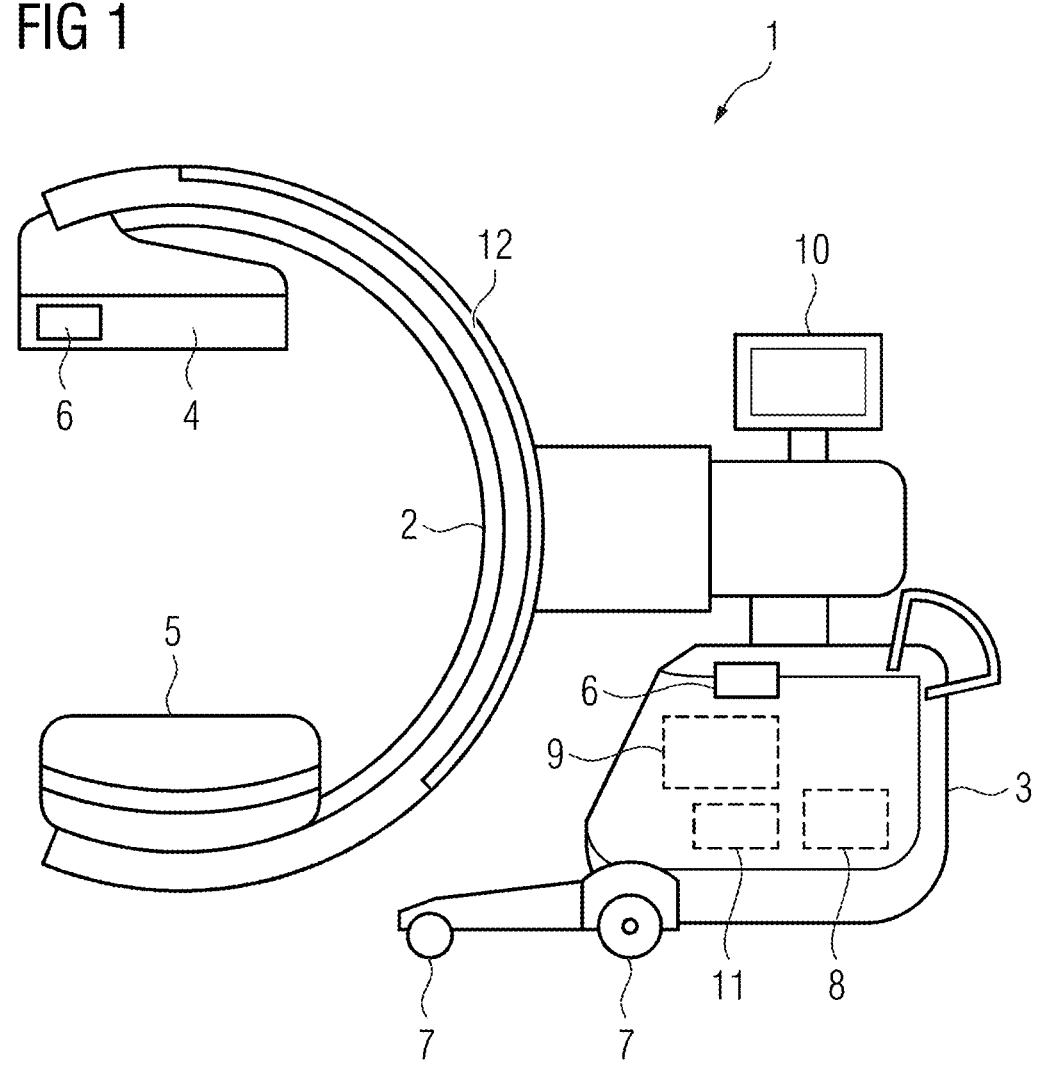
FIG. 1 depicts a view of an example of a mobile X-ray device with a C-arm, which is suitable for carrying out the method.

FIG. 1 depicts a mobile X-ray device 1 suitable for carrying out the method described herein. The mobile X-ray device 1 has a device trolley 3 that may be moved at will with wheels 7 driven by a motor and a C-arm 2 that may be automatically adjusted with regard to its position and/or its angle of inclination. For mobility and adjustability, the mobile X-ray device has a plurality of drives (not shown), which may be automatically or semi-automatically actuated. The drives customarily supply encoder values, which show the corresponding movement or adjustment. While encoder values may be unquestioningly used as an indicator of the implemented positioning in mobile X-ray devices from the prior art, the mobile X-ray device 1 is embodied for carrying out the monitoring method by which, for example, the encoder values supplied by the drives are checked. Similarly, it is possible to check by the method whether the actuated movement and the movement actually carried out are identical.

The C-arm 2 holds an X-ray source 5 and an X-ray detector 4, which are arranged at opposite ends of the C-arm 2. The C-arm 2 shown may be rotated, for example, along its circumference, and turned about a plurality of axes. X-ray radiation emitted by the X-ray source 5 falls onto the X-ray detector 4, which is embodied for capturing X-ray image data. The mobile X-ray device 1 is actuated by a system control unit 8. One inertial measurement unit 6 respectively is arranged on the device trolley 3 and on the C-arm 2 (for example, as shown, directly on the X-ray detector 4). More than two inertial measurement units may also be present. Each inertial measurement unit 6 includes at least three acceleration sensors, which are disposed orthogonally to each other respectively, for acquiring translational movements in three spatial axes and three angular rate sensors mounted orthogonally to each other for acquiring rotating movements in three spatial axes. It is possible to determine positions and angles of inclination therefrom by way of corresponding evaluations of the sensor data by an evaluation unit 9. The respective inertial measurement unit 6 is embodied, in particular, for acquiring sensor data in respect of the component on which it is arranged, for example, the inertial measurement unit, arranged on the C-arm 2 or the X-ray detector 4, for acquiring sensor data in respect of the C-arm 2 or the X-ray detector 4. In particular, the coordinate systems are also registered with each other for this purpose.

In addition, the mobile X-ray device 1 has a determining unit 11, which is configured to compare the evaluated position and/or the evaluated angle of inclination with specified values and to determine deviations. The specified values may be formed by encoder values or by values derived from the encoder values. The specified values may also be formed by target values input automatically or by an operator. In addition, the mobile X-ray device 1 has at least one output unit for outputting an indication when the deviations overshoot a threshold value. This may be a monitor 10, which displays, for example, a deviation as a numerical value or graphic or outputs a warning message in words, image, or color. An acoustic or haptic output may also be present, for example, by a loudspeaker or joystick (not shown).

FIG. 2 shows the acts of a method for automatically monitoring a position or change in position and/or an angle of inclination or change in angle of inclination of a component of a medical mobile X-ray device 1 using at least one inertial measurement unit 6, which method minimizes the problems described above.

The method is automatically carried out, for example, during a movement/adjustment or during an activation of the mobile X-ray device 1. It may be provided that the method is carried out continuously during operation of the mobile X-ray device 1 or is purposefully started or triggered at the beginning of a movement/adjustment and is terminated directly or a period of time after the end of the movement.

Figure 6:
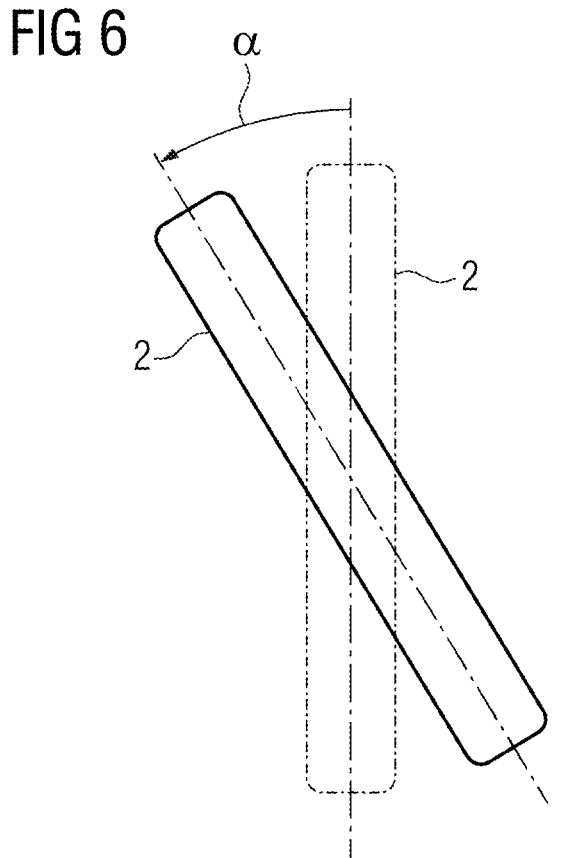
FIG. 6 depicts an example of a view of a change in the angle of inclination in the case of a C-arm of a mobile X-ray device.

FIG. 6 shows, by way of example, a change in angle of inclination a in the case of a C-arm 2 of a mobile X-ray device 1 by tilting the C-arm 2 about an axis located in the C-arm plane.

Figure 7:
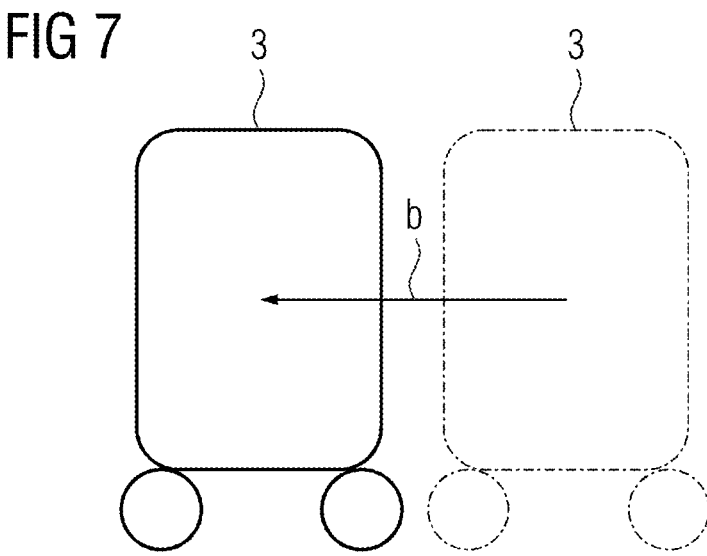
FIG. 7 depicts an example of a view of a change in the position of a device trolley of a mobile X-ray device.

FIG. 7 shows, by way of example, a translational movement of the device trolley 3 of the mobile X-ray device about a translational length b from a first position into a second position.

Returning to FIG. 2, in act 20, at least one measured value of at least one sensor of the inertial measurement unit 6 is acquired. This may be carried out, in particular, during a movement or adjustment of at least one component of the mobile X-ray device 1 or also in order to record spontaneous changes in position (due to collisions) or those resulting over a relatively long period (due to vibrations). For example, for the case of an adjustment of the angle of inclination of the C-arm 2 (due to a single- or multi-axis tilting or rotation) at the beginning of the adjustment, the three angular rate sensors are activated for acquiring the rotating movements in three spatial axes of the inertial measurement unit 6 arranged on the C-arm 2 and capture measured values throughout the duration of the adjustment. Another example is that the three acceleration sensors of the inertial measurement unit 6 arranged on the device trolley 3 capture measured values for the duration of a translational or curving movement of the device trolley 3. A further example is recording measured values of the three angular rate sensors of the inertial measurement unit 6 arranged on the C-arm 2 while the device trolley of the mobile X-ray device is being moved to be able to thus identify vibrations of the C-arm 2. A further example is recording measured values of the three angular rate sensors of the inertial measurement unit 6, arranged on the C-arm 2, directly after the end of the adjustment of the C-arm, likewise to be able to identify vibrations of the C-arm 2. A further example is recording measured values of the three acceleration sensors of the inertial measurement unit 6, arranged on the device trolley

3, over a relatively long period while the mobile X-ray device is operating in order to be able to identify collisions.

In act 21, the at least one measured value or the (large number of) measured value(s) of the inertial measurement unit 6 is evaluated, for example, with regard to at least one position or change in position and/or with regard to at least one angle of inclination or change in angle of inclination of the component (for example, C-arm or device trolley). This is carried out, for example, by an evaluation unit 9 (arranged, for example, on/in the mobile X-ray device or part of the IMU). By way of example, for the case of the C-arm 2, the angle of inclination adopted after the end of the movement (tilting) and/or its change in angle of inclination during tilting are determined: an integration of the three angular speeds of the angular rate sensors supplies, based on a reference point, the orientation (of the inertial measurement unit 6 and owing to the fixed arrangement, accordingly also of the C-arm 2) in the space. In the example of an inertial measurement unit arranged on the device trolley, a position or a change in position (of the inertial measurement unit and owing to the fixed arrangement, accordingly also of the device trolley) are determined during the course of the movement from the measured value(s) captured during the translational movement of the device trolley 3: an integration of the linear accelerations, after compensating acceleration due to gravity, supplies the linear speed and a further integration, the position in the space based on a reference point.

In act 22, the evaluated position/change in position or the at least one evaluated angle of inclination/change in angle of inclination are then compared with at least one specified value, for example, with the encoder value or the position or the angle of inclination of the component ascertained from the encoder value. The encoder value is supplied, for example, by the corresponding drive, which actuates the movement or tilting, for example, by a first drive therefore, which drives the toothed belt, which moves the C-arm, or by one of the wheel drives, which drives the wheels 7 of the device trolley 3. If the movement is an interaction of a plurality of drives, for example, in the case of a robotic arm with a plurality of axes, then a specified value is used accordingly from the encoder values of the drives, which value is ascertained from the interaction of the drives. The specified value may also be formed by a target value of the position or the angle of inclination, which was specified automatically or manually, for example.

At least one deviation of the evaluated position and/or of the at least one evaluated angle of inclination from the at least one specified value is determined during the comparison.

In act 23, following this, (e.g., if the deviation overshoots a threshold value), an indication or a display is output. This may be a display in writing or graphics on a monitor 10 and/or an acoustic, optical, or haptic warning (for example, by loudspeaker, flashing light, joystick, etc.). The operator may also receive an indication of an error or a prompt to carry out a correction in the operating program (for example, organ program). The threshold value may be automatically selected or be pre-set by an operator.

In addition, the movement may also be automatically terminated, for example, when the threshold value is overshot in a very short amount of time (e.g., collision suspected) or a function of the mobile X-ray device (for example, application of X-ray radiation) or the entire mobile X-ray device may be stopped.

FIGS. 3 to 6 show various specific embodiments of the method. The values of the three acceleration sensors of the inertial measurement unit 6 arranged on the device trolley 3 are acquired in FIG. 3 in act 40 during a traversing movement of the device trolley 3. The measurement starts and ends with the movement. The positions or changes in position (for example, from A to B or 1.5 m linear travel, etc.) are ascertained from the values of the acceleration sensors in act 41. These are then compared in act 42 with the encoder values gathered from the drives of the wheels 7 of the device trolley or values ascertained from the encoder values (for example, if a plurality of drives interact) and a deviation is determined. If the deviation overshoots a threshold value (for example, 5 cm or 3%), then in act 43 the monitor 10 shows the operator that a deviation has occurred, possibly together with a warning signal or a flashing light or the like. The method may be used here to check the precision of previously stored park-position values of the mobile X-ray device, which were captured in a previously defined park position of the device trolley, and if required, to correct them.

During an adjustment or tilting of the C-arm 2, the values of the three angular rate sensors of the inertial measurement unit 6, which is arranged on the C-arm 2, are captured in FIG. 4 in act 30. The measurement starts with the beginning of the adjustment and ends when the adjustment ends. In act 31, the angle of inclination or the changes in angle of inclination of the C-arm 2 are ascertained in three dimensions (for example, a tilting about 10° in the x-axis from 0° to +10° and 0° in the y- and z-axes) from the values of the angular rate sensors. These are then compared in act 32 with the encoder values gathered from the drives, which adjust the C-arm, and a deviation is determined. If the deviation(s) overshoot(s) a threshold value (for example, 1° or 10%), then, in act 33, the monitor 10 shows or warns the operator that a deviation has occurred. In addition, a recalibration, (e.g., of the encoder values), is carried out in act 34 on the basis of the deviation. Alternatively, or additionally, instead of the deviating encoder values, (e.g., in an organ program or other displays), the values which are based on the inertial measurement unit are used instead of the encoder values, or at least one correction of the values used is carried out.

A trigger signal, which starts the method, takes place in act 19 in FIG. 5. This may be triggered, for example, by the activation of the mobile X-ray device or the beginning of a movement or adjustment of a component. If a deviation, which overshoots a threshold value, is ascertained during the course of the method, then emission of X-ray radiation or an X-ray photograph or another function of the mobile X-ray device is blocked in act 25, for example until a recalibration or a correction has been carried out.

The method may be used to detect vibrations of the mobile X-ray device or to detect the effects of vibrations (for example, a decrease in the positional accuracy therefore) and possibly to correct them. Thus, for example, a plurality of measurements of the inertial measurement unit may be carried out one after the other, after movement has been carried out ("resting" or vibrating mobile X-ray device) and deviations relating to the previous measurement respectively may be determined (e.g., the specified values are formed by the previous measured values or positions or angles of inclination ascertained therefrom).

A further example of vibration monitoring includes, for example, carrying out a plurality of measurements of the inertial measurement unit of the C-arm one after the other during a traversing movement of the device trolley and determining deviations in relation to a particular preliminary measurement (e.g., the specified values are formed by a particular preliminary measured value or angles of inclination ascertained therefrom). A further example of vibration monitoring is, for example, that a plurality of measurements of the inertial measurement unit of the C-arm are carried out one after the other during a traversing movement of the device trolley and deviations in relation to the previous measurement respectively are determined (e.g., the specified values are formed by the previous measured value respectively or angles of inclination ascertained therefrom).

The inertial measurement units may also have magnetometers (e.g., magnetic field sensors) and global navigation system sensors (GNSS), for example, for determining the integration constants, for improving the accuracy, and for correcting the zero point and long-term drift of the other sensors.

An inertial measurement unit 6 may also be used to carry out a plausibility check during the respective movement or adjustment in that the actually executed movement is compared (manually or automatically, by a program) with the addressed movement and in the case of a deviation, is stopped. If, for example, the device trolley 3 is actuated to carry out a straight translational movement and if the inertial measurement unit 6 on the device trolley 3 (using the acceleration sensors) then detects that the device trolley is actually traveling on a curve, then either the movement may be stopped, or an indication may be output to the operator.

The inertial measurement unit 6 may be used for an automatic internal calibration in that the actual zero point, [e.g., the neutral position of the C-arm therefore; (0°; 0°)], is measured with the aid of the corresponding sensors and the corresponding encoder values of the drives are stored and set as a reference. The accuracy is considerably higher than the accuracy with a known manual procedure. If the inertial measurement unit 6 of the C-arm 2 and the inertial measurement unit 6 of the device trolley 3 are connected, it is possible to compensate potential unevenness in the floor.

Aa described, the inertial measurement unit may be used to check the validity of the encoder values. A known problem of C-arms is that the toothed belt, which moves the C-arm, sometimes slips through and the C-arm is not moved, although the drive (and therewith the encoder values) have registered a movement. The neutral position of the C-arm then has to be recalibrated. A deviation of this kind may be detected with the aid of the values of the inertial measurement unit and a calibration may then be automatically triggered.

A further possible use includes monitoring the position of the device trolley in the case of manual movement of the mobile X-ray device by an inertial measurement unit in order to facilitate a manual repositioning by the operator.

The disclosure may be briefly summarized as follows. For checking the positional accuracy, a method for automatically monitoring a position and/or an angle of inclination of a component 2, 3 of a medical mobile X-ray device 1, (e.g., of a C-arm 2), using at least one inertial measurement unit 6 is provided. The mobile X-ray device 1 has a device trolley 3 and a C-arm 2, which may be adjusted with regard to its position and/or its angle of inclination, and the at least one inertial measurement unit 6 is arranged on the mobile X-ray device 1. The method includes acquiring at least one measured value of the inertial measurement unit 6. The method further includes evaluating the at least one measured value of the inertial measurement unit 6 with regard to a position and/or an angle of inclination of the component 2, 3 of the mobile X-ray device 1, (e.g., of the C-arm 2). The method further includes comparing the evaluated position and/or the at least one evaluated angle of inclination with at least one specified value and determining deviations from the at least one specified value. The method further includes outputting an indication or a display when the deviation overshoots a threshold value.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for automatically monitoring a position and/or an angle of inclination of a component of a medical mobile X-ray device, wherein the medical mobile X-ray device has a device trolley, and wherein an at least one inertial measurement unit is arranged on the medical mobile X-ray device, the method comprising:

acquiring at least one measured value of the inertial measurement unit;

evaluating the at least one measured value of the inertial measurement unit with regard to the position or a change in position and/or the angle of inclination or a change in angle of inclination of the component of the medical mobile X-ray device, wherein the medical mobile X-ray device has at least one drive for adjusting the position and/or the angle of inclination of the component;

comparing the position or the change in position and/or the angle of inclination or the change in the angle of inclination with at least one specified value, wherein the at least one specified value is based on at least one encoder value of the at least one drive of the medical mobile X-ray device in respect of the position and/or the angle of inclination of the component;

determining a deviation from the at least one specified value;

displaying, by a display of the medical mobile X-ray device, an indication when the deviation overshoots a threshold value, wherein the display provides the position and/or the angle of inclination of the component of the medical mobile X-ray device, and wherein the display is controlled using the at least one encoder value of the at least one drive; and correcting the display based on the deviation and/or a recalibration of the at least one encoder value.

2. The method of claim 1, wherein the method is automatically triggered by activation of the at least one drive.

3. The method of claim 1, wherein the component is formed by a C-arm, wherein the inertial measurement unit is arranged on the C-arm, and wherein the at least one measured value is evaluated with regard to an angle of inclination of the C-arm.

4. The method of claim 1, wherein the component is formed by the device trolley, wherein the at least one inertial measurement unit is arranged on the device trolley, and wherein the at least one measured value is evaluated with regard to a position of the device trolley.

5. The method of claim 1, further comprising:

outputting an acoustic warning, an optical warning, a haptic warning, or a combination thereof when the deviation overshoots the threshold value.

6. The method of claim 1, wherein the at least one specified value is formed by measured values, preliminary to the method, of the at least one inertial measurement unit with regard to the position and/or the angle of inclination of the component of the medical mobile X-ray device.

7. The method of claim 1, wherein the deviation is used as a basis for image processing.

8. The method of claim 7, wherein the image processing is a three-dimensional (3D) reconstruction image processing or a panoramic image processing.

9. The method of claim 1, wherein the acquiring, the evaluating, and the comparing are carried out at least twice in succession with a time interval between the acquiring, the evaluating, and the comparing, and wherein each specified value is formed by the at least one measured value of a previous measurement, respectively.

10. The method of claim 9, wherein the method is carried out continuously as long as the medical mobile X-ray device is in operation and/or being moved.

11. The method of claim 1, wherein the medical mobile X-ray device is a C-arm device.

12. The method of claim 11, wherein the C-arm device holds an X-ray detector at one end and an X-ray source at another end, and wherein the inertial measurement unit is arranged indirectly or directly on the X-ray detector.

13. The method of claim 1, wherein the at least one drive is a motor-driven drive arranged on wheels of the device trolley of the medical mobile X-ray device.

14. A medical mobile X-ray device comprising:

a device trolley;

an adjustable C-arm on which an X-ray detector and an X-ray source are arranged;

at least one inertial measurement unit arranged on the device trolley and/or the adjustable C-arm, wherein the at least one inertial measurement unit is configured to acquire sensor data;

at least one drive configured to adjust at least one position and/or an angle of inclination of the device trolley and/or the adjustable C-arm;

a control unit configured to:

evaluate the sensor data with regard to the at least one position or change in position and/or the angle of inclination or a change in angle of inclination of the device trolley and/or the adjustable C-arm;

compare the position or the change in position and/or the angle of inclination or the change in the angle of inclination with at least one specified value, wherein the at least one specified value is based on at least one encoder value of the at least one drive of the medical mobile X-ray device in respect of the position and/or the angle of inclination of the adjustable C-arm or the device trolley; and determine a deviation from the at least one specified value; and a display configured to display an indication when the deviation overshoots a threshold value, wherein the display is configured to provide the position and/or the angle of inclination of the adjustable C-arm or the device trolley, wherein the display is configured to be controlled using the at least one encoder value of the at least one drive, and wherein the display is configured to be corrected based on the deviation and/or a recalibration of the at least one encoder value.

15. The medical mobile X-ray device of claim 14, wherein the adjustable C-arm holds the X-ray detector at one end and the X-ray source at another end, and wherein the at least one inertial measurement unit is arranged indirectly or directly on the X-ray detector.

16. The medical mobile X-ray device of claim 15, wherein the at least one inertial measurement unit is arranged indirectly or directly on the device trolley.

17. The medical mobile X-ray device of claim 14, wherein the at least one inertial measurement unit comprises a first inertial measurement unit arranged on the device trolley and a second inertial measurement unit arranged on the adjustable C-arm.

18. The medical mobile X-ray device of claim 14, wherein the at least one drive is a motor-driven drive arranged on wheels of the device trolley of the medical mobile X-ray device.

\* \* \* \* \*